United States Patent
Lanning et al.

(10) Patent No.: US 7,531,159 B2
(45) Date of Patent: May 12, 2009

(54) METHOD FOR EXTRACTING $H_2S$ FROM SOUR GAS

(75) Inventors: Robert A. Lanning, The Woodlands, TX (US); F. Stephen Brusso, Houston, TX (US); Gary W. Sams, Tulsa, OK (US)

(73) Assignee: National Tank Company, Houston, TX (US)

( * ) Notice: Subject to any disclaimer, the term of this patent is extended or adjusted under 35 U.S.C. 154(b) by 295 days.

(21) Appl. No.: 11/493,240

(22) Filed: Jul. 26, 2006

(65) Prior Publication Data

US 2008/0023373 A1  Jan. 31, 2008

(51) Int. Cl.
- *B01D 19/00* (2006.01)
- *B01D 19/02* (2006.01)
- *C01B 17/05* (2006.01)
- *C10L 3/10* (2006.01)
- *C12P 3/00* (2006.01)

(52) U.S. Cl. ......... 423/573.1; 423/576.2; 423/DIG. 17; 435/168; 435/266; 48/127.3; 48/127.5; 48/127.7; 96/177; 95/242

(58) Field of Classification Search ............. 423/573.1, 423/576.2, DIG. 17; 435/168, 266; 48/127.3, 48/127.5, 127.7; 96/177; 95/242
See application file for complete search history.

(56) References Cited

U.S. PATENT DOCUMENTS

| | | | |
|---|---|---|---|
| 2,274,658 A * | 3/1942 | Booth | 210/703 |
| 3,348,683 A | 10/1967 | Wikdahl | |
| 4,838,434 A | 6/1989 | Miller et al. | |
| 4,997,549 A | 3/1991 | Atwood | |
| 5,112,375 A | 5/1992 | Brown | |
| 5,143,525 A * | 9/1992 | Sotirianos | 95/242 |
| 5,192,423 A | 3/1993 | Duczmal et al. | |
| 5,476,573 A * | 12/1995 | Hirose et al. | 202/197 |
| 5,522,510 A | 6/1996 | Luttrell et al. | |
| 5,900,046 A * | 5/1999 | Taylor | 95/242 |
| 6,056,934 A | 5/2000 | Carlsen et al. | |
| 6,162,284 A | 12/2000 | Mitchell et al. | |
| 6,521,201 B1 * | 2/2003 | Seriwala | 423/567.1 |
| 6,576,029 B2 | 6/2003 | West | |
| 6,656,249 B1 | 12/2003 | Buisman et al. | |
| 6,773,492 B1 | 8/2004 | West | |
| 2003/0068813 A1 * | 4/2003 | Rietschel et al. | 435/301.1 |

FOREIGN PATENT DOCUMENTS

| | | |
|---|---|---|
| WO | WO 92/10270 | 6/1992 |
| WO | WO 96/30110 | 10/1996 |

OTHER PUBLICATIONS

Intl Search Rpt, Jan. 17, 2008, PCT Office.
Written Opinion, Jan. 17, 2008, PCT Office.

* cited by examiner

*Primary Examiner*—Timothy C Vanoy
(74) *Attorney, Agent, or Firm*—Gable Gotwals

(57) ABSTRACT

This invention teaches a process that includes extraction of gas in which the presence of foam results in the carry over in the outlet gas stream of excessive liquids and/or solids, including the steps of injecting the foam laden gas stream tangentially into a cyclonic separator having an axial gas outlet and a liquid outlet, under conditions in which the inlet stream is subjected to at least about 150 G's, the outlet gas being substantially liquids/solids free and the outlet liquid stream being conveyed for disposal or further processing.

9 Claims, 1 Drawing Sheet

METHOD FOR EXTRACTING H₂S FROM SOUR GAS

REFERENCE TO PENDING APPLICATIONS

This application is not based upon any pending domestic or international patent applications.

FIELD OF THE INVENTION

This invention relates to a process for the removal of sulfur compounds from a gas flow stream that is treated in a bioreactor and an absorber, the output of the absorber is fed into a centrifugal separator for separation of gas and foam, the residue of which is fed to a decanter providing a sulfur slurry from which elemental sulfur may be obtained, the resultant gas stream being substantially free of sulfur.

BACKGROUND OF THE INVENTION

Hydrogen sulfide gas has a number of undesirable properties. At low concentrations (i.e., less than 10 parts per million), the gas has a strong odor of "rotten eggs". Paradoxically, at concentrations greater than 100 parts per million (ppm), the gas can no longer be smelled, but it will induce dizziness. Concentrations of greater than about 500 ppm can be fatal to humans. Hydrogen sulfide can also be oxidized to sulfur dioxide, a chemical that contributes to acid rain.

Hydrogen sulfide ($H_2S$) gas can be released by a variety of sources. Biologically-generated hydrogen sulfide is generally the product of anaerobic digestion of organic matter, and can be released by sewage treatment facilities, solid waste landfill, paper mill waste, cattle feed lots, poultry farms, and other industries employing anaerobic digestion for processing. $H_2S$ is also released by oil drilling operations, oil refinery operations, and operations utilizing geothermal brines, such as for power generation.

Biological technologies are frequently used for $H_2S$ abatement. Sulfur bacteria (i.e., bacteria that are able to metabolize sulfur compounds) can be utilized in biofilter or bioscrubber reactors to oxidize $H_2S$ to sulfates. Biofilter and bioscrubber plants are normally designed to produce elemental sulfur. In this process, $H_2S$ gas is passed over the bioreactor bed under aerobic conditions, leading to reduction of the $H_2S$ to elemental sulfur that is deposited intracellularly and extracellularly as a solid in clumps or granules. This elemental sulfur is mechanically removed periodically from the bioreactor bed. The deposited sulfur, once removed, may be disposed of or utilized in industrial and/or agricultural processes.

The invention herein relates to processing gas streams to remove hydrogen sulfide using an alkaline solution containing Thiobaccilus bacteria (Thiopaq). The alkaline solution contains solid particles of elemental sulfur in the 1 to 20 micron size range. The presence of the sulfur particles is essential to proper operation of the biological $H_2S$ removal process. An unfortunate side effect of most of these biological sulfur removal processes is formation of foam that can be detrimental to the proper operation of the process.

In treating gas streams, especially natural gas streams, it is important that $H_2S$ not be carried to the downstream equipment or pipelines because of possible fouling or corrosion. The formation of foam in the processing equipment can be caused by excessive sulfur solids concentration, flashing of dissolved gas during pressure reduction, counter current gas/solution flow, agitation, shear through spray nozzles and pumps, presence of surfactants and other causes.

Conventional separation devices are not effective in handling this type of foam. The invention herein applies high G forces to the foam containing gas stream using a cyclonic separation device. It has been determined that high G forces can be used to cause the foam to collapse and allow the sulfur and solution to properly separate from exiting gas streams. Laboratory pilot testing has confirmed that at a certain level of G forces the most persistent foams could be broken and the gas stream cleanly separated from the solids and liquids in the foam. This level of G forces was not intuitive, and is an order of magnitude more G's than would typically be expected.

For additional information relating to biological gas sweetening systems and processes, reference may be had to the following previously issued United States patents.

| Patent Number | Inventor | Title |
| --- | --- | --- |
| 4,838,434 | Miller et al. | Air Sparged Hydrocyclone Flotation Apparatus and Methods For Separating Particles From A Particulate Suspension |
| 4,997,549 | Atwood | Air-Sparged Hydrocyclone Separator |
| 5,112,375 | Brown | Radial Vane Demisting System In A Separator For Removing Entrained Droplets From A Gas Stream |
| 5,192,423 | Duczmal et al. | Apparatus and Method For Separation Of Wet Particles |
| 5,522,510 | Luttrell et al. | Apparatus For Improved Ash and Sulfur Rejection |
| 6,162,284 | Mitchell et al. | Separator For Gases, Liquids and Solids From A Well |
| 6,773,492 | West | System Employing A Vortex Tube For Separating An Entrained Liquid Component From A Gas Stream |
| 6,576,029 | West | System For Separating An Entrained Liquid Component From A Gas Stream |

BRIEF SUMMARY OF THE INVENTION

This invention relates to a system for treating a natural gas stream having an entrained liquid (usually water) component and entrained hydrogen sulfide ($H_2S$). Essential components of the system includes a bioreactor, an enclosed treatment vessel that typically operates at or about atmospheric pressure, a counter flow absorber and at least one centrifugal separator. A source of natural gas as produced in the petroleum industry is typically available at a high pressure, such as 2000 to 5000 PSIG. This high pressure gas flows through a pressure reduction flow control where the pressure is reduced to about 1200 PSI. This gas may contain foam created as a result of water and liquid hydrocarbon content and by the friction reducing soaps used in well boreholes. The reduced pressure gas, frequently having foam entrained therein, flows tangentially into an inlet centrifugal separator where it is subjected to rapid cyclonic action so that the heavier components are moved towards the wall of the vessel with the lighter or gas components moving towards the interior of the whirling flow stream, the lighter components passing out the top of the inlet centrifugal separator while the heavier or essentially liquid component passes out of the inlet centrifugal separator through liquid outlet piping.

The heavier, liquid component from inlet centrifugal separator is fed to the inlet of a flash vessel that has a liquid level therein with a gas collection area above the liquid level. In the flash vessel liquid and gas components are allowed to separate with a liquid slurry discharge that feeds into a bioreactor. Gas from the inlet centrifugal separator passes into a counter current absorber in which $H_2S$ is absorbed out of the gas component, that is, the $H_2S$ containing gas flows upwardly in the absorber contacting downwardly flowing recycled liquid. From the absorber liquid solution flows through a pressure reduction valve to a flash vessel. Within the flash vessel the liquid and gas components are allowed to separate. As a consequence of the pressure reduction the separation process results in the creation of a heavy foam which passes with the gas components into the flash vessel. The gas component is passed into a tangential inlet of an intermediate centrifugal separator where high gas velocity produces a strong centrifugal separation force of about 150 G's. The whirling stream with its high G force collapses the foam and separates the liquid component of the inlet stream from the gas component and passes the liquid component downwardly within the centrifugal separator while the less heavy gas component migrates to the interior of the whirling stream to form a vortex that passes out through an axial gas outlet. The high G forces within intermediate centrifugal separator serve to effectively remove any foam component associated with the liquid stream, the bubbles of the foam collapsing under the high G forces to form gas that passes out through the outlet while the liquid component, having all foam extracted therefrom goes through a level control valve that serves to maintain a liquid level in the bottom portion of the intermediate centrifugal separator, and then the slurry merges with the slurry discharge from the flash vessel to flow into the bioreactor.

The $H_2S$ removable aspect of the present system is primarily achieved as a consequence of reactions taking place within the absorber while the conversion of $H_2S$ to elemental sulfur takes place essentially in the bioreactor. The slurry output from the flash vessel passes into the interior of the bioreactor. Also introduced into the bioreactor is NaOH, air and nutrients. Within the bioreactor are structures that provide large surface area per unit volume. These structures provide support medium systems that are coated with sulfur consuming microorganisms such as a commercially available type available under the trademark "THIOPAQ". As water and nutrients are circulated through the absorber, a biological reaction occurs in which the $H_2S$ contained in the original gas stream is oxidized to form elemental sulfur and some sulfates. The result of the biological oxidation step is a liquid output that communicates with a decanter. The decanter separates the inlet components to provide elemental sulfur. Residuary gas from the decanter is returned to the interior of the bioreactor.

Thus the system of the invention provides a process for the removal of sulfur compounds, including specifically $H_2S$. The system makes use of high gravitational separation forces available in a centrifugal separator to alleviate the problem that frequently arises from the tendency of an absorber to produce a foamy discharge in the process of $H_2S$ removal.

The essence of the invention herein can be summarized as follows: A liquid component of the system having a commercially available microorganism called THIOPAQ is constantly recirculated in the system, flowing from a flash vessel, through a bioreactor, a solution pump, through a downwardly passing current in an absorber and, after pressure reduction, back to a flash vessel. $H_2S$ is absorbed by the THIOPAQ microorganisms, primarily in the absorber. This system has, in some instances, been difficult to commercially operate because the biological process characteristically produces large amounts of foam that is difficult to separate from the recycled stream, especially if traditional gravitational separation is attempted. This invention provides a method and system of making this biological gas sweetening process commercially viable by employing one or more high G force centrifugal separators critically placed in the system. Further, it has been determined, unexpectedly, that centrifugal separation forces of at least about 150 G's are necessary to adequately deal with the foam problem.

A better understanding of the invention will be obtained from the following detailed description of the preferred embodiments taken in conjunction with the drawings and the attached claims.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawing. The drawing is a flow diagram of a system for making use of the method of this invention for extracting $H_2S$ from natural gas that employs a biological gas sweetening process and includes improved methods of controlling foam that is typically produced in biological gas sweetening processes.

DETAILED DESCRIPTION OF A PREFERRED EMBODIMENTS

Figure 1:
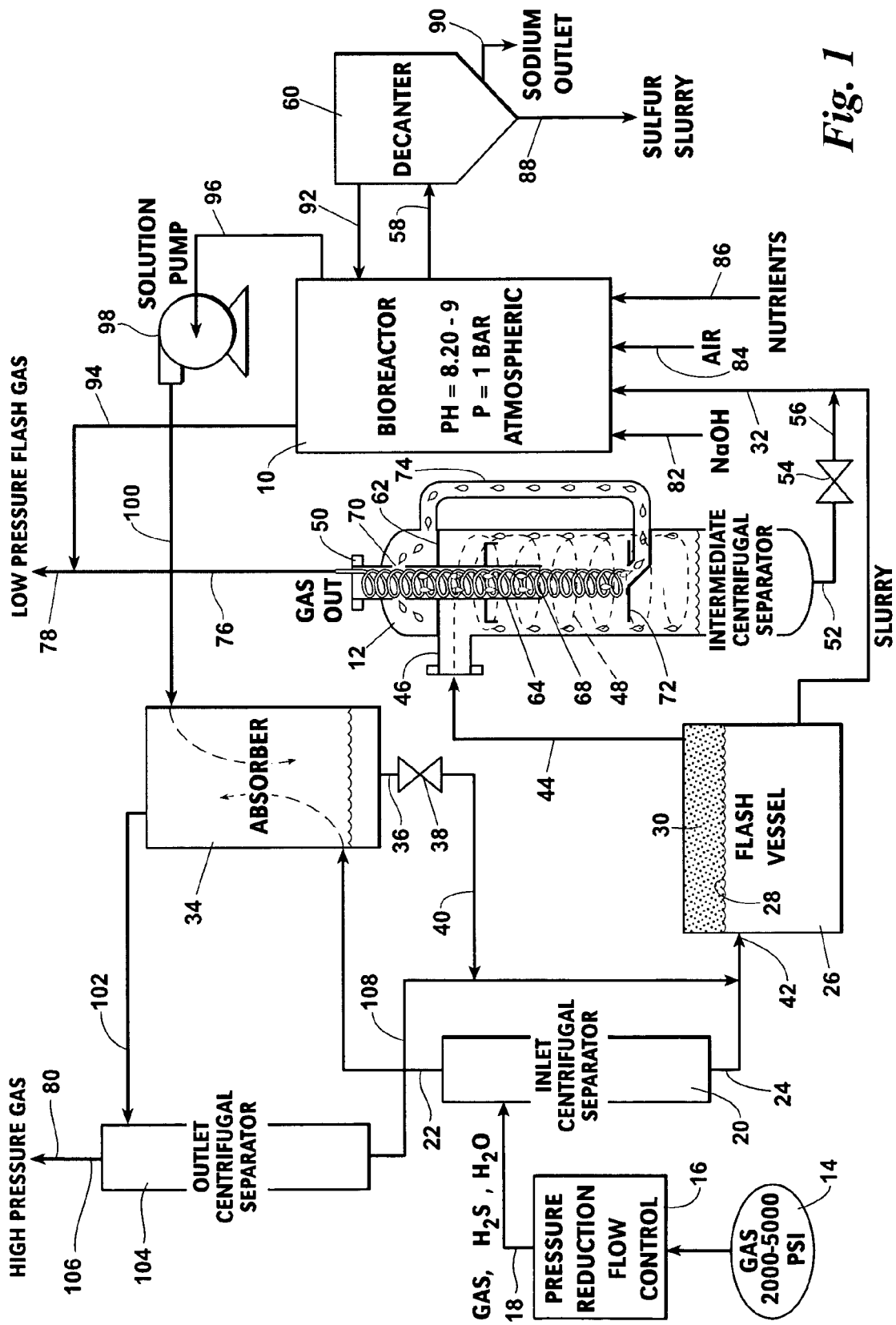

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements shown by the drawings are identified by the following numbers:

| | |
|---|---|
| 10 | Bioreactor |
| 12 | Intermediate centrifugal separator |
| 14 | Gas source |
| 16 | Pressure reduction flow control |
| 18 | Conduit |
| 20 | Inlet centrifugal separator |
| 22 | Gas outlet piping |
| 24 | Liquid outlet piping |
| 26 | Flash vessel |
| 28 | Liquid level |
| 30 | Gas collection area |
| 32 | Liquid slurry discharge |
| 34 | Counter current absorber |
| 36 | Liquid outlet |
| 38 | Pressure reduction valve |
| 40 | Conduit |
| 42 | Liquid inlet |
| 44 | Gas conduit |
| 46 | Inlet |
| 48 | Swirling stream |
| 50 | Gas outlet |
| 52 | Liquid outlet |
| 54 | Level control valve |
| 56 | Conduit |
| 58 | Inlet |
| 60 | Decanter |
| 62 | Baffle |
| 64 | Vortex finder |
| 68 | Vortex |
| 70 | Circumferential outlet |
| 72 | Flat baffle |
| 74 | Return conduit |
| 76 | Conduit |
| 78 | Low pressure flash gas conduit |
| 80 | High pressure gas conduit |
| 82 | NaOH inlet |
| 84 | Air inlet |
| 86 | Nutrients inlet |

-continued

| | |
|---|---|
| 88 | Sulfur slurry outlet |
| 90 | Sodium outlet |
| 92 | Gas recycle conduit |
| 94 | Bioreactor gas outlet |
| 96 | Outlet conduit |
| 98 | Pump |
| 100 | Outlet conduit |
| 102 | Absorber outlet |
| 104 | Outlet centrifugal separator |
| 106 | Gas outlet |
| 108 | Liquid outlet |

Referring to the drawing, a flow diagram illustrates one system in which the invention herein may be employed. Illustrated in the flow diagram is a system for treating a natural gas stream having an entrained liquid (usually water) component and entrained hydrogen sulfide ($H_2S$). Essential components of the illustrated system for practicing the invention includes a bioreactor, an enclosed treatment vessel that typically operates at or about atmospheric pressure, a counter flow absorber and at least one centrifugal separator.

Centrifugal separators of the type used in this invention are commercially available products manufactured and sold by NATCO Group, headquartered in Houston, Tex., USA and sold under the trademark "PORTA-TEST WHIRLY-SCRUB".

A source of gas, such as natural gas as produced in the petroleum industry, and that is available at a high pressure is indicated by the numeral 14. The gas source 14 may be such as an entire gas producing field in which the gas is gathered by a pipeline system. On the other hand, the gas source 14 may be a single well or may be a flow stream that is a part of a refinery operation. Gas source 14 is typically at a high pressure, such as 2000 to 5000 PSIG. This high pressure gas flows through a pressure reduction flow control 16 where the pressure is reduced to about 1200 PSI. Gas from source 14 may contain foam created as a result of water and liquid hydrocarbon content and by the friction reducing soaps used in well boreholes. The reduced pressure gas, frequently having foam entrained therein, passes through conduit 18 and then tangentially into an inlet centrifugal separator 20. In the inlet centrifugal separator 20 the gas stream is subjected to rapid cyclonic action in which the components of the stream are subjected to gravitational forces so that the heavier components are moved towards the wall of the vessel with the lighter or gas components moving towards the interior of the whirling flow stream, the lighter components passing out the top of the inlet centrifugal separator through gas outlet piping 22 while the heavier or essentially liquid component passes out of inlet centrifugal separator 20 through liquid outlet piping 24.

The heavier or liquid component from inlet centrifugal separator 20 is passed by liquid outlet piping 24 to the inlet of a flash vessel 26 that has a liquid level 28 therein with a gas collection area 30 above the liquid level. In flash vessel 26 liquid and gas components are allowed to separate with a liquid slurry discharge 32 that feeds into bioreactor 10. For reasons that will be more apparent subsequently, the gas collection area 30 is typically filled with foam that can be, in some instances, as heavy as typical aerated shaving cream.

Gas from outlet piping 22 from inlet centrifugal separator 20 passes into a counter current absorber 34 in which $H_2S$ is absorbed out of the gas component. That is, $H_2S$ containing gas from gas outlet piping 22 flows upwardly in absorber 34 contacting downwardly flowing liquid recycled from bioreactor 10. A level of recycled liquid is maintained in absorber 34. From absorber 34 liquid solution flows through outlet 36 and a pressure reduction valve 38 and through conduit 40 to a liquid inlet 42 of flash vessel 26. Within flash vessel 26 the liquid and gas components are allowed to separate. As a consequence of the pressure reduction produced by valve 38 the separation process results in a heavy foam which passes with the gas components through the liquid inlet 42 into flash vessel 26. The gas component passes out through gas conduit 44 under high pressure and through a tangential inlet 46 of intermediate centrifugal separator 12. Tangential inlet 46 introduces the gas from flash vessel 26 at a high velocity tangentially into the interior of intermediate centrifugal separator 12. The high gas velocity produces a strong centrifugal separation force of about 150 G's. The swirling gas stream is indicated by the numeral 48 within separator 12. The whirling stream with its high G force collapses the foam and separates the liquid component of the inlet stream from the gas component and passes the liquid component downwardly within the centrifugal separator while the less heavy gas component migrates to the interior of the whirling stream within the centrifugal separator to form a vortex that passes out through axial gas outlet 50. The high G forces within intermediate centrifugal separator 12 serve to effectively remove any foam component associated with the liquid stream, the bubbles of the foam collapsing under the high G forces to form gas that passes out through outlet 50 while the liquid component, having all foam extracted therefrom, passes out of intermediate centrifugal separator 12 through liquid outlet 52.

The liquid slurry component from intermediate centrifugal separator 12 that flows through piping 52 goes through a level control valve 54 that serves to maintain a liquid level, as indicated, in the bottom portion of intermediate centrifugal separator 12, and then the slurry passes through conduit 56 to merge with the slurry from slurry discharge conduit 32 to flow into bioreactor 10.

Intermediate centrifugal separator 12 is shown with an optional self-contained recirculation feature. The upper end of the vessel 12 above inlet 46 is separated from the lower interior portion of the separator by a baffle 62. The centrifugal separator has an axially positioned vortex finder tube 64 that receives the swirling gas component vortex 68 produced by the rapidly swirling stream within the separator. In an upper portion of vortex finder 64, positioned above baffle 62, is a circumferential outlet opening 70. The whirling action within centrifugal separator 12 continues within vortex finder 64 so any liquid contained within the whirling gas is forced against the interior wall of vortex finder 64 and flows out through circumferential outlet opening 70 and through return conduit 74 back into the interior of the centrifugal separator 12. Liquid component contained within vortex 68 and that is returned through return conduit 74 collects on a flat baffle 72 and flows downwardly into the lower, liquid collection interior portion of intermediate centrifugal separator 12.

Gas emanating from outlet 50 of intermediate centrifugal separator 12 passes by conduits 76 and 78 for storage or further use. High pressure gas passes from the system through high pressure gas outlet 80 as will be described subsequently. The gas passing through low pressure flash gas conduit 78 is essentially $H_2S$ free. The flash gas at 78 is therefore dry, that is substantially liquid-free and more important, is substantially free of $H_2S$, and is therefore considered to be "sweet" gas.

The $H_2S$ removable aspect of the present system is primarily achieved as a consequence of reactions taking place within absorber 34 while the conversion of $H_2S$ to elemental sulfur takes place essentially in bioreactor 10. As previously stated, the slurry output from flash vessel 30 passes by way of conduit 32 into the interior of bioreactor 10. Also introduced into bioreactor 10 is NaOH through inlet 82, air through an inlet 84 and nutrient through an inlet 86. Within bioreactor 10 are structures that provide large surface area per unit volume. These can be achieved in a number of ways. One system that is frequently employed is the use of items commercially called "Shell Paques" that have been perfected by Royal Dutch Shell Corp. These ceramic elements provide support medium systems that are coated with sulfur consuming microorganisms such as a type commercially available under the trademark "THIOPAQ" owned by Paques B.V. Corporation of the Netherlands. As water and nutrients are circulated through the Shell Paques, a biological reaction occurs in which the $H_2S$ contained in the original gas stream is oxidized to form elemental sulfur and some sulfates. Elemental sulfur is a desired end product. The result of the biological oxidation step in bioreactor 10 is a liquid output through conduit 58 that communicates with decanter 60. Liquid from outlet 52 of intermediate centrifugal separator 12, after having passed through level control valve 54, flows through conduit 56 that meets with conduit 32 and is thus cycled to bioreactor 10. Decanter 60 separates inlet components to provide sulfur slurry through outlet 88 while elemental sulfur is extracted through a sodium outlet 90. Residuary gas from decanter 60 is returned to the interior of bioreactor 10 by way of a gas recycle conduit 92.

Substantially sulfur-free flash gas is provided at the bioreactor gas outlet 94 that is combined with gas outlet from intermediate centrifugal separator 12 in conduit 78 that provides low pressure flash gas.

Overflow liquid component from bioreactor 10 is withdrawn by way of outlet conduit 96 and pump 98 and fed by conduit 100 into absorber 34. Gas from absorber 34 is fed by outlet 102 to an outlet centrifugal separator 104. In separator 104, as with centrifugal separators 12 and 20, centrifugal force is employed to separate the liquid and foam components from the gas stream. Substantially liquid and foam free gas passes through outlet piping 106 to provide high pressure gas through high pressure gas conduit 80. The liquid, foam or heavier component discharge from outlet centrifugal separator 104 flows through conduit 108 and commingles with the liquid and foam from inlet centrifugal separator 20 and passes into flash vessel 26 through liquid inlet 42.

Thus the system illustrated in the drawing provides a process for the removal of sulfur compounds, including specifically $H_2S$. The system makes use of high gravitational separation forces available in a centrifugal separator to alleviate the problem that frequently arises from the tendency of an absorber 34 to produce a foamy discharge in the process of $H_2S$ removal.

The employment of a vortex finder tube 64 with a circumferential outlet opening 70 above a baffle 62 and with a return conduit 74 is an optional provision of intermediate centrifugal separator 12 and are not indispensable to the practice of the basic invention described in this paper. Similar recycle systems can optionally be employed with inlet centrifugal separator 20 or with an outlet centrifugal separator to be subsequently described without changing the basic concepts of the invention. The use of at least one centrifugal separator capable of producing a centrifugal separation force of at least about 150 G's is considered essential to the practice of the invention to effectively deal with foam as is customarily produced in most biological systems of extracting $H_2S$ from natural gas, however the details of construction of the centrifugal separator or separators employed are not considered to be critical to the practice of the basic invention.

The essence of the invention herein can be summarized as follows: A liquid component of the system having a commercially available microorganism called THIOPAQ is constantly recirculated in the system, flowing from flash vessel 26, through bioreactor 10, solution pump 98, through a downwardly passing current in absorber 34 and, after pressure reduction in reducer 38, back to flash vessel 26. $H_2S$ is absorbed by the THIOPAQ microorganisms, primarily in absorber 34. This system has, in some instances, been difficult to commercially operate because the biological process characteristically produces large amounts of foam that is difficult to separate from the recycled stream, especially if traditional gravitational separation is attempted. This invention provides a method and system of making this biological gas sweetening process commercially viable by employing one or more high G force centrifugal separators critically placed in the system. Further, it has been determined, unexpectedly, that centrifugal separation forces of at least about 150 G's are necessary to adequately deal with the foam problem.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claims, including the full range of equivalency to which each element thereof is entitled.

What is claimed is:

1. For use in a process that includes a foam laden gas stream in which the presence of foam results in the carry over of liquids and/or solids, the method comprising:
    injecting the foam laden stream tangentially into a cyclonic separator having a gas outlet and a liquid outlet under pressurized conditions in which the gas stream is subjected to centrifugally generated gravitational force sufficient to substantially collapse the foam, providing an outlet gas stream that is substantially liquids, solids and foam free.

2. The method provided in claim 1 in which said gravitational force generated in said cyclonic separator is at least about 150 G's.

3. The method provided in claim 1 in which the foam laden gas stream results from a hydrogen sulfide removal process.

4. The method provided in claim 1 in which the foam laden gas stream results from a process that uses an alkaline solution containing bacteria.

5. The method provided in claim 1 in which the foam laden gas stream is caused by the interaction of gas, water, elemental sulfur and/or surface active agents.

6. A method of extracting $H_2S$ and entrained liquid components from a pressured natural gas stream comprising the steps of:
    passing the pressured natural gas stream into contact with a recirculated liquid current having entrained therein a $H_2S$ consuming microorganism to provide a treated gas stream;
    passing said treated gas stream through pressure reduction resulting in a foam laden gas stream;
    passing said foam laden gas stream under pressurized conditions into a centrifugal separator in which the foam is subjected to centrifugally generated gravitational forces sufficient to substantially collapse the foam; and
    extracting an outlet gas stream that is substantially free of $H_2S$ and liquid components.

7. A method according to claim 6 in which the gravitational force generated in said centrifugal separator is at least about 150 G's.

8. A method according to claim 6 in which the liquid current is treated in a bioreactor by which elemental sulfur is removed.

9. A method according to claim 8 in which said bioreactor employs surface area structures coated with sulfur fixation organisms.

* * * * *